(12) United States Patent
Goergen et al.

(10) Patent No.: US 10,863,967 B2
(45) Date of Patent: Dec. 15, 2020

(54) PHOTOACOUSTIC PROBE

(71) Applicant: Purdue Research Foundation, West Lafayette, IN (US)

(72) Inventors: Craig Jonathan Goergen, West Lafayette, IN (US); Gurneet Sangha, West Lafayette, IN (US); Evan Phillips, West Lafayette, IN (US); Nicholas James Hale, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 515 days.

(21) Appl. No.: 15/830,716

(22) Filed: Dec. 4, 2017

(65) Prior Publication Data
US 2018/0192993 A1    Jul. 12, 2018

Related U.S. Application Data

(60) Provisional application No. 62/429,320, filed on Dec. 2, 2016.

(51) Int. Cl.
*A61B 8/00* (2006.01)
*A61B 5/00* (2006.01)
*G10K 15/04* (2006.01)
*G01N 29/24* (2006.01)
*G10K 11/00* (2006.01)

(52) U.S. Cl.
CPC .......... *A61B 8/4218* (2013.01); *A61B 5/0073* (2013.01); *A61B 5/0095* (2013.01); *A61B 8/4444* (2013.01); *G01N 29/2418* (2013.01); *G10K 11/004* (2013.01); *G10K 15/046* (2013.01)

(58) Field of Classification Search
CPC ... A61B 5/0073; A61B 5/0095; A61B 8/4218; A61B 8/4444; G01N 29/2418; G10K 11/004; G10K 15/046
See application file for complete search history.

(56) References Cited

U.S. PATENT DOCUMENTS

| | | | | |
|---|---|---|---|---|
| 2013/0312527 A1* | 11/2013 | Lomenzo, Jr. | ......... | G01N 29/04 73/632 |
| 2015/0272444 A1* | 10/2015 | Maslov | ............... | A61B 5/7278 600/407 |

OTHER PUBLICATIONS

Wang, Z., et al, "A new design of light illumination scheme for deep tissue photoacoustic imaging." Optics express 20.20, 2012, pp. 22649-22659.

(Continued)

*Primary Examiner* — Amelie R Davis
(74) *Attorney, Agent, or Firm* — Purdue Research Foundation

(57) ABSTRACT

Disclosed herein is a photoacoustic tomography (PAT) probe to direct light to various regions within the tissue of interest to improve image quality and remove cumbersome artifacts at their source. Particularly, a rotating PAT probe and method of using thereof to improve the photoacoustic penetration depth and signal to noise ratio in biological samples. Signal intensity at region of interest is increased by fine-tuning the fiber orientation with respect to the ultrasound transducer. Additional PA filter is used to prevent in vivo probe-skin artifacts.

14 Claims, 15 Drawing Sheets

(56) References Cited

OTHER PUBLICATIONS

Yu, J., et al, "A light illumination enhancement device for photoacoustic imaging: in vivo animal study." IEEE transactions on ultrasonics, ferroelectrics, and frequency control 64.8, 2017, pp. 1205-1211.
Nie, L., et al, "Photoacoustic tomography through a whole adult human skull with a photon recycler." Journal of biomedical optics 17.11, 2012, pp. 110506-01-110506-03.
Jaeger, M., et al, "Reduction of background in optoacoustic image sequences obtained under tissue deformation." Journal of biomedical optics 14.5, 2009, pp. 054011-01-054011-10.
Jaeger, M., et al, "Clutter elimination for deep clinical optoacoustic imaging using localised vibration tagging (LOVIT)." Photoacoustics 1.2, 2013, pp. 19-29.
Singh, M., et al, "Photoacoustic-guided focused ultrasound (PAFUSion) for identifying reflection artifacts in photoacoustic imaging." Photoacoustics 3.4, 2015, pp. 123-131.
Singh, M., et al, "In vivo demonstration of reflection artifact reduction in photoacoustic imaging using synthetic aperture photoacoustic-guided focused ultrasound (PAFUSion)." Biomedical optics express 7.8, 2016, pp. 2955-2972.

\* cited by examiner

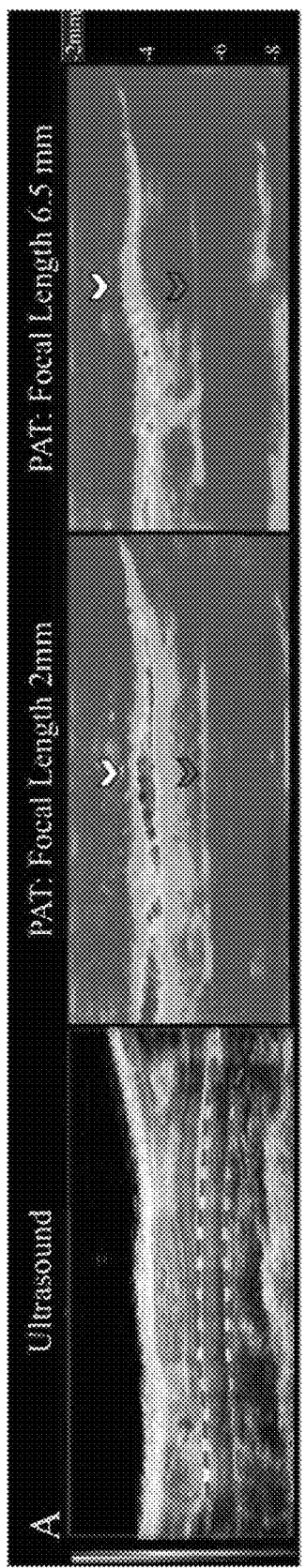
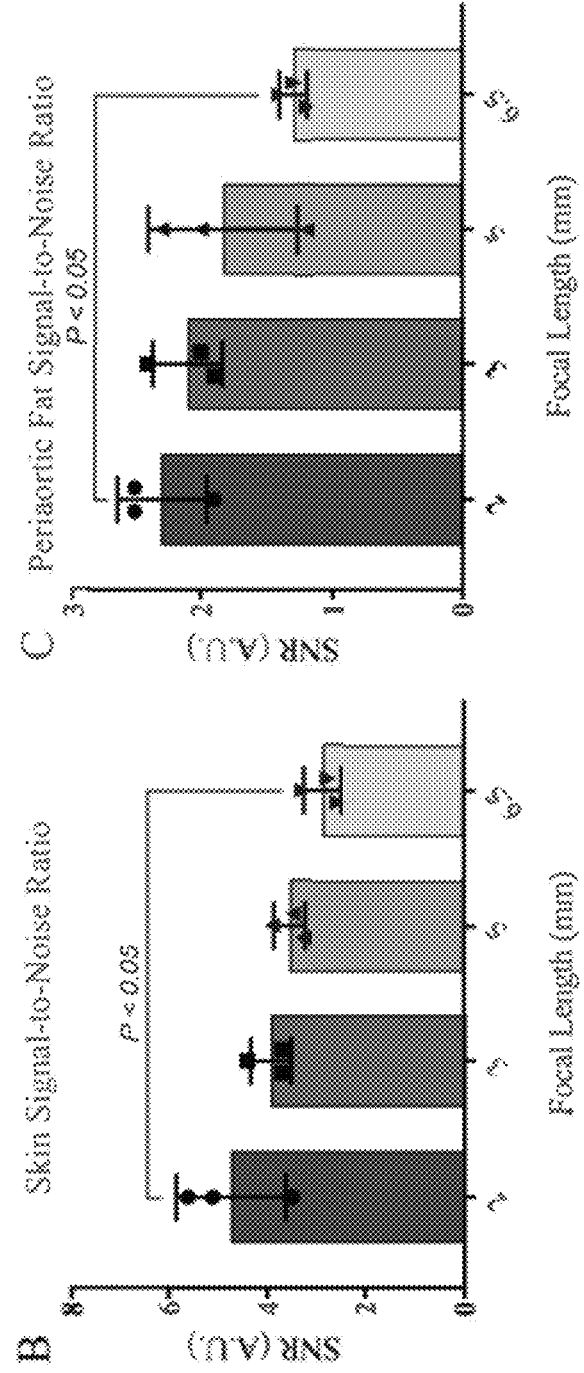
FIG. 12A, FIG. 12B, & FIG. 12C

PHOTOACOUSTIC PROBE

CROSS REFERENCE

The application claims the benefit of U.S. provisional application 62/429,320, filed on Dec. 2, 2016. The contents therein are expressly incorporated herein entirely.

TECHNICAL FIELD

The present application relates to a probe used in a photoacoustic arrangement for inspection of tissue of a subject or biologically excised samples.

BACKGROUND

This section introduces aspects that may help facilitate a better understanding of the disclosure. Accordingly, these statements are to be read in this light and are not to be understood as admissions about what is or is not prior art.

Atherosclerosis contributes to 50% of the deaths in the Western world. Manifestations of atherosclerosis appear in a wide variety of diseases, including coronary artery disease, ischemic stroke, and peripheral artery disease. Patients who suffer from atherosclerotic-related diseases experience an extensive range of complications that are associated with significant morbidity and mortality. For instance, myocardial infarction and ischemic stroke account for 84.5% of all cardiovascular deaths in the world. Moreover, blockage in the lower extremities due to peripheral artery disease can cause discomfort at rest due to intermittent claudication and pain during exercise due to critical limb ischemia, affecting over 200 million people worldwide. Diagnosing, treating, and managing atherosclerotic-related disease represent a significant cost.

Established modalities have been used to study and diagnose atherosclerosis, but their limitations restrict the study, diagnosis, and monitoring of early atherosclerotic lesions in high-risk patients. For example, magnetic resonance angiography can be used to characterize lipid in plaques, but its high cost and long scan times make it impractical for use in high throughput imaging of patients. X-ray techniques cannot easily characterize plaque composition and involve ionizing radiation. Ultrasound (US) is economical, rapid, and can provide geometric and hemodynamic information of the vasculature, but like X-ray imaging, does not provide compositional information to improve plaque characterization. Optical techniques have been developed to better characterize lipid lesions, but limited penetration depth limits their use.

Currently available vascular imaging modalities are not ideal for the diagnosis and characterization of atheroscleroticrelated diseases due to their inherent limitations. For instance, long acquisition times, high cost, use of exogenous contrast, and minimal to high invasiveness are all factors that restrict image monitoring in high-risk patients in a cost- and time-effective manner. It is also important to develop imaging techniques for differentiating stable plaque from vulnerable plaque (i.e. large lipid core with a thin fibrous plaque) to better assess therapeutic and surgical intervention strategies. Even with the most recent technology available, many vulnerable atherosclerotic lesions remain undetected, leading to a need for new definitions and risk assessment strategies. Unfortunately, the recurrence rate for atherosclerotic-related diseases is between 10-20% in the first 12 months after treatment. This marks the need to develop better imaging techniques to cost effectively monitor atherosclerosis progression before, during, and after therapeutic (e.g. statins, fibrates, niacin) and surgical (e.g. endarterectomy, angioplasty, stenting, bypass) interventions.

PAT has been shown to provide real-time compositional information of tissue without the need for exogenous contrast agents and with superior depth of penetration compared to conventional optical techniques. These orthodox optical barriers are surpassed as PAT does not rely on conventional ballistic photons, but rather detects acoustic waves that are thermoelastically produced by photon-tissue interactions. Therefore, PAT can provided useful information that complements current clinical imaging modalities, thus emphasizing the capability of this technology to improve medical care. These characteristics highlight the potential of the technology to be used for a variety of biomedical applications ranging from lipid imaging, tumor margin detection, and peripheral nerve imaging.

While PAT has shown great potential, there are still certain biological barriers that limit its use to its full capacity. For instance, applications for high-resolution noninvasive lipid-based imaging are limited to roughly 3 mm due to subcutaneous fat absorbers, as well as the intrinsic light attenuation due to optical properties of tissue. Taken together, there is still an engineering need to optimize this technology to fully utilize the attributes of this technique There is, therefore an unmet need for a novel imaging modality to rapidly, noninvasively, and cost-effectively locate and quantify atherosclerotic plaque composition in vivo. Accordingly, such novel imaging modality may be applied to other medical conditions to make relevant diagnosis or analysis.

This application file contains at least one drawing executed in color. Copies of this patent or patent application publication with color drawing(s) will be provided by the Office upon request and payment of the necessary fee.

SUMMARY OF THE INVENTION

This disclosure provides a photoacoustic tomography (PAT) bracket. The bracket comprises a translating ultrasound transducer holder; and two rotating fiber arms coupled to the ultrasound transducer holder. Each fiber arm is configured to hold a fiber optic bundle and juxtaposed with respect to the ultrasound transducer holder at a pivoting point, and the fiber arm is further configured to rotate the fiber optic bundle and laser light projections thereof such that the laser projections intersect at a selective focal depth of a subject of interest below the bracket.

In some embodiment, the aforementioned ultrasound transducer holder is configured to provide linear translation of the ultrasound transducer to tune the pivot point in which the fiber optic bundles articulate.

In some embodiment the aforementioned fiber arms are configured to rotate the fiber optic bundle angle to converge the laser light projections at various depths of the subject of interest to optimize the optical contrast in the subject of interest.

In some embodiment the aforementioned ultrasound transducer holder is configured to linearly translate the ultrasound transducer up and down with respect to the subject of interest.

In some embodiment the aforementioned each of the two fiber arms is configured to articulate about the ultrasound transducer holder by angular motion, linear motion or the combination of both motions.

In some embodiment the aforementioned PAT bracket further comprising force sensors coupled to the ultrasound transducer holder and configured to provide force information between the ultrasound transducer and the skin of the subject of interest.

In some embodiment the aforementioned force information is used to move the bracket in order to optimize photoacoustic signal generated by the subject of interest and captured by the ultrasound transducer.

In some embodiment the aforementioned PAT bracket further comprising a photoacoustic filter that is configured to redirect laser light reflected from the skin of the subject of interest back toward the skin while allowing ultrasound waves to pass through.

In some embodiment the aforementioned PAT bracket further comprising an ultrasound gel incorporating photo reflectors to reflect light back onto the skin of the subject of interest.

In some embodiment the aforementioned subject of interest is a biological sample to be analyzed for its compositional information.

In some embodiment the aforementioned biological sample is selected from the group consisting of atherosclerosis plaques, cancer tissues, body fluids and peripheral nerve tissues and their compositional information at various focal length is used for diagnosing their relative pathological progression.

In some embodiment the aforementioned fiber optic bundles are producing fixed wavelength lasers.

This disclosure further provides a method to generate optimum photoacoustic signals to a subject of interest. The method comprising:

a. providing a photoacoustic tomography (PAT) bracket comprising: a translating ultrasound transducer holder; and two rotating fiber arms coupled to the ultrasound transducer holder, wherein each fiber arm is configured to hold a fiber optic bundle and juxtaposed with respect to the ultrasound transducer holder at a pivoting point, and said fiber arm is further configured to rotate said fiber optic bundle and laser light projections thereof;

b. applying a fixed wavelength light through the fiber optic bundle while rotating the fiber arms and translating the ultrasound transducer holder to fine tune the pivoting point;

c. acquiring photoacoustic images at different focal length of the subject of interest to obtain images with increased photon density at various depths;

d. applying digital image processing algorithms to concatenate all images obtained in c in order to reconstruct the photoacoustic image with improved photon density throughout the image; and e. optionally providing a light reflecting material over the ultrasound transducer to remove any reflection artifact that is potentially obscuring the image at the region of interest, wherein said artifact is induced due to photoacoustic effect at the ultrasound transducer face.

In some embodiment the aforementioned fixed wavelength is selected from the group of 1100 nm, 1210 nm, 1250 nm, and 1400 nm.

In some embodiment the aforementioned light reflecting material is a photoacoustic filter.

In some embodiment the aforementioned the subject of interest are lipid tissues e.g. atherosclerosis plaques, various cancer tissues, body fluids, peripheral nerve tissues or polyethylene-50 (PE-50) tubes for ex vivo validation of focal length are proportional to the tissue penetration ability of PAT probe.

In some embodiments the aforementioned range[s] of the focal length is about 2 mm, 3 mm, 5 mm, 6.5 mm, or about 10 mm+for maximum photon density within the subject of interest.

These and other features, aspects and advantages of the present invention will become better understood with reference to the following figures, associated descriptions and claims.

BRIEF DESCRIPTION OF DRAWINGS

FIG. 12: In vivo Validation Results: Subcutaneous fat and infrarenal periaortic fat were imaged in apoE$^{-/-}$ mice to show increased PAT signal intensity when tuning focal length from 6.5 mm to 2 mm (FIG. 12A). We can clearly observe increased signal-to-noise SNR in the subcutaneous fat (white arrow) and periaortic fat (red arrow). Infrarenal aorta is outlined in red dotted line. Quantitative assessment shows statistically significant ($p<0.05$) increase in subcutaneous signal-to-noise SNR of 62% (FIG. 12B), and statistically significant ($p<0.05$) increase in periaortic fat of signal-to-noise SNR of 77% (FIG. 12C).

DETAILED DESCRIPTION

Figure 1:
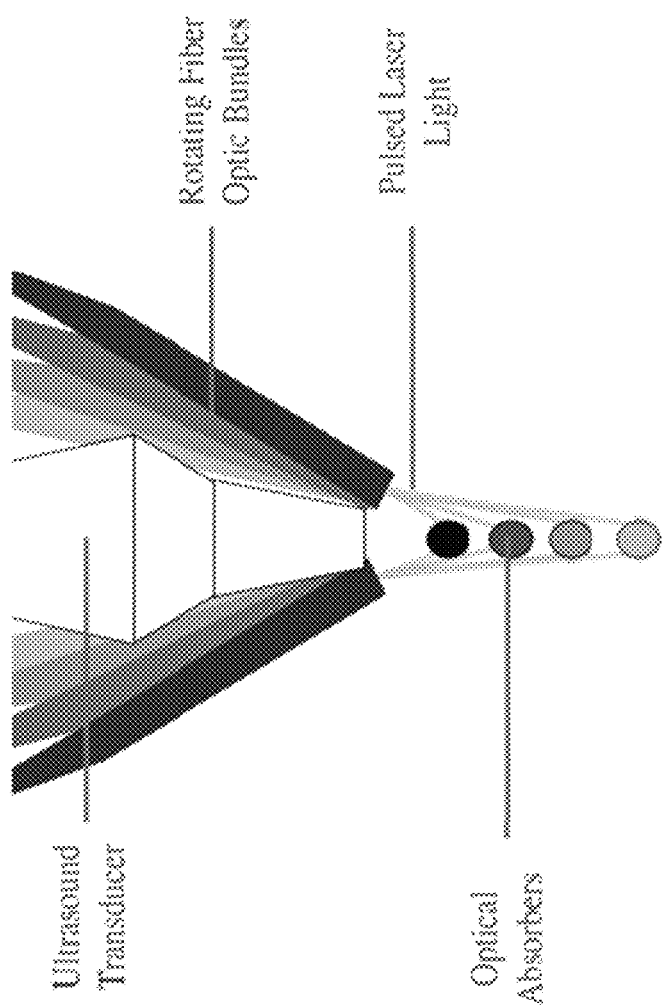
FIG. 1: Schematic showing of PAT holder concept. Rotating fiber optic bundles allows the user to target optical absorbers at varying depths within tissue in order to increase optical density and, as a result, improve penetration depth and signal to noise ratio.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

As used herein, "PAT" refers to photoacoustic tomography.

As used herein, "focal length" is defined as the distance where the light converges with respect to the fiber optic bundles.

As disclosed herein, any fixed wavelength light at a given time travels through a fiber optic bundle. These fixed wavelengths can be 1100 nm light for targeting blood samples, 1210 nm light for targeting lipid, and 1250 or 1400 nm as an off-resonance control.

A novel imaging arrangement capable of rapidly, noninvasively, label-free, and cost-effectively locating and quantifying tissue composition ex vivo and in vivo is disclosed herein. In cases of atherosclerosis, this arrangement can longitudinally monitor plaque formation, which represents an advancement that could decrease the cost of therapeutic development research for atherosclerosis. Furthermore, the improved imaging techniques could enhance patient therapy by providing plaque characterization information, which would be useful when determining treatment options. The novel arrangement disclosed herein, can also be used for other tissue characterization such as blood sample, other body fluids, cancer tissues, lipid tissues, and peripheral nerve tissues. The disclosed motorized photoacoustic tomography probe can be used as label-free improvement in image quality, and provide superior penetration depth compared to current optical techniques and better spatial resolution than magnetic resonance angiography without the use of ionizing radiation. The disclosed system can obtain structural, hemodynamic, and compositional information to enhance tissue characterization.

Atherosclerosis plaque formation begins with an insult to the arterial endothelial layer, causing intimal permeability to low-density lipoproteins (LDL, which are oxidized and induce complicated biological pathways that result in complex plaque formation with heterogeneous composition. Fibrotic plaques, for example, are of particular importance as they are rupture-prone and have a high probability to form a thrombus that can induce myocardial infarctions, ischemic strokes, or decrease peripheral blood flow. It is therefore evident that characterizing plaque composition plays a vital role in the diagnosis of atherosclerosis, as some lesions may not need advanced therapies or surgical intervention where others do. Thus, a rapid, noninvasive, label-free method to characterize lipid lesions will allow for a better understanding of plaque progression and eventually help guide personalized patient care.

By coupling an ultrasound (US) system and a laser, high resolution structural, hemodynamic, and compositional information can be obtained of the vasculature in a rapid, noninvasive, label-free manner.

PAT utilizes a non-ionizing pulsed laser in conjunction with US to obtain biologically relevant information from the tissue of interest. Some of the delivered energy is absorbed and converted into heat, leading to thermoelastic expansion followed by creation of a pressure transient that then propagates as an acoustic wave. An US transducer is then used to detect the emission of these acoustic waves. The magnitude of the ultrasonic PA signal is proportional to the energy deposition at that location, revealing physiologically specific optical absorption contrast. These small changes in pressure can be measured and used to create a 2D image based on the location of the absorbers. The approached described herein increases penetration depth and decreases artifacts.

Figure 6:
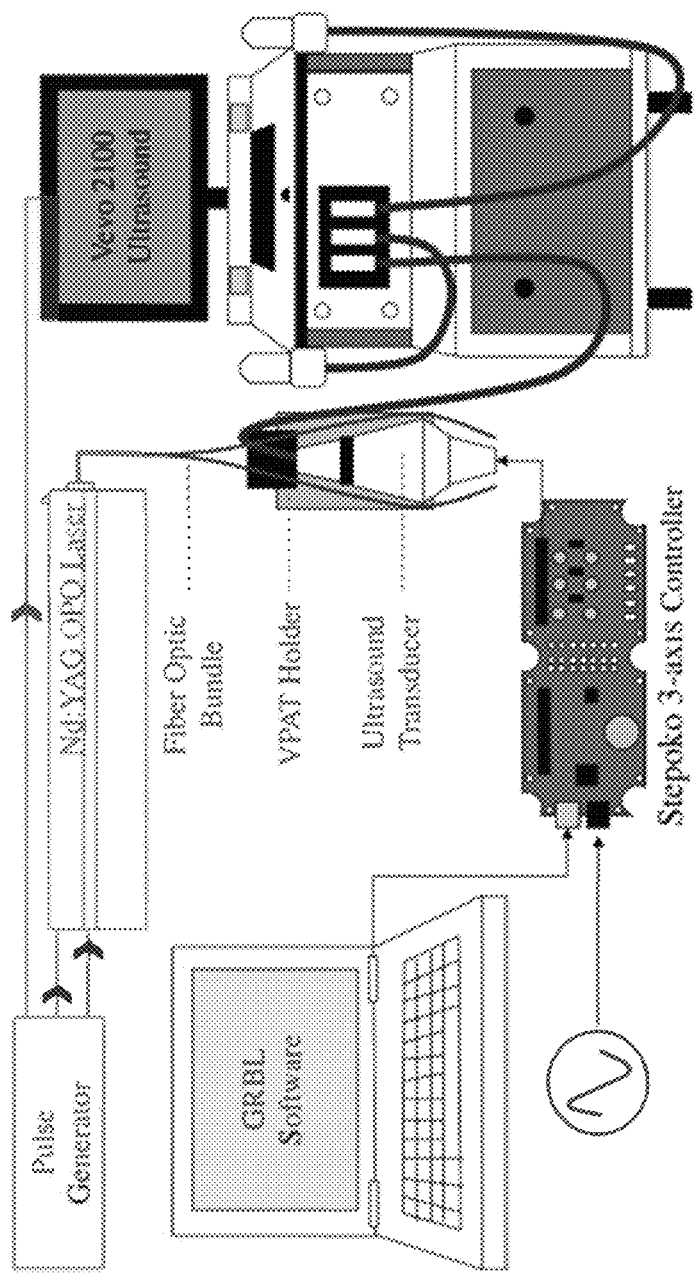
FIG. 6: Schematic of PAT system setup with PAT holder. Pulse generator synchronized laser pulse output, and ultrasound and PAT image acquisition. GRBL software was used to control the Stepoko 3-axis controller, which allowed fine translation of the ultrasound transducer and rotation of the fiber optic bundles.

A schematic PAT system with PAT holder is exemplified in FIG. 6, with the understanding that equivalent exchange of suitable devices of each component is within the contemplation of this disclosure. Pulse generator synchronized laser pulse output, and ultrasound and PAT image acquisition. GRBL software was used to control the Stepoko 3-axis controller, which allowed fine translation of the ultrasound transducer and rotation of the fiber optic bundles.

Figure 2:
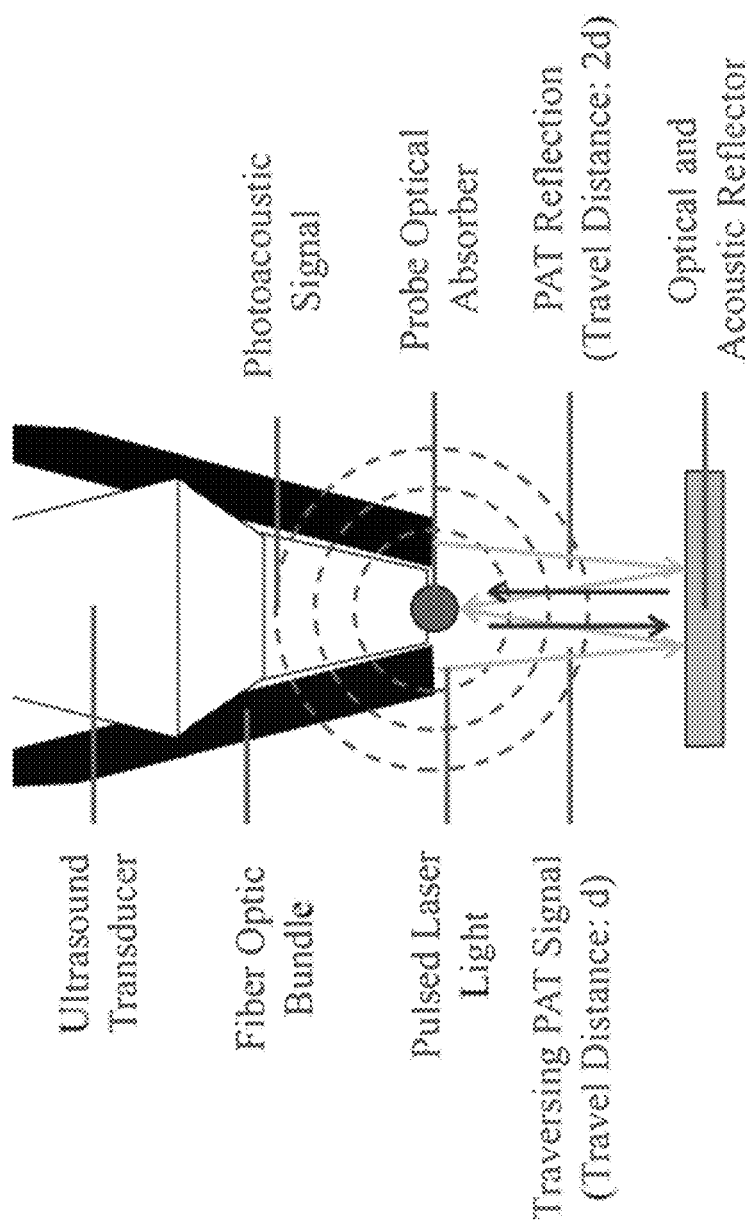
FIG. 2: Schematic showing origin of PAT reflection artifact. Light from the fiber optic bundles reflects off of the optical reflector and induces the photoacoustic effect at the PAT probe face. This PAT signal then travels distance d distance down towards the acoustic reflector and travels another distance d distance up towards the ultrasound transducer. The PAT system, therefore, registers the acoustic wave as traveled $2d$, creating an artifact that can appear in the region of interest.

Particularly, PA imaging according to the teachings of the present disclosure can be obtained with reference to FIGS. 1 and 2. With reference to FIG. 1, it shows the disclosed PAT holder concept. Rotating fiber optic bundles allow the user to target optical absorbers at varying depths within tissue in order to increase optical density and as a result, improves penetration depth and signal to noise ratio. Typically, a PA probe with articulating arms can be positioned against the sample or subject of interest. The PA probe includes two fiber optic bundles each coupled to a laser (or a common laser), as well as a US transducer centrally positioned between the two fiber optic bundles. The fiber optic bundles are coupled to arms that can articulate as discussed below.

FIG. 2 is a schematic showing of PAT reflection artifact origin. Light from the fiber optic bundles reflects off of the optical reflector and induces the photoacoustic effect at the PAT probe face. This PAT signal then travels distance d distance down towards the acoustic reflector and travels another distance d distance up towards the ultrasound transducer. The PAT system, therefore, registers the acoustic wave as traveled $2d$, creating an artifact that can appear in the region of interest.

To avoid such artifact, the PA probe may also include a PA filter that is configured to redirect the laser light reflected from the skin back toward the skin while allowing US waves to pass through. The PA probe may also have a US gel as an interface between the probe and the skin.

Figure 3:
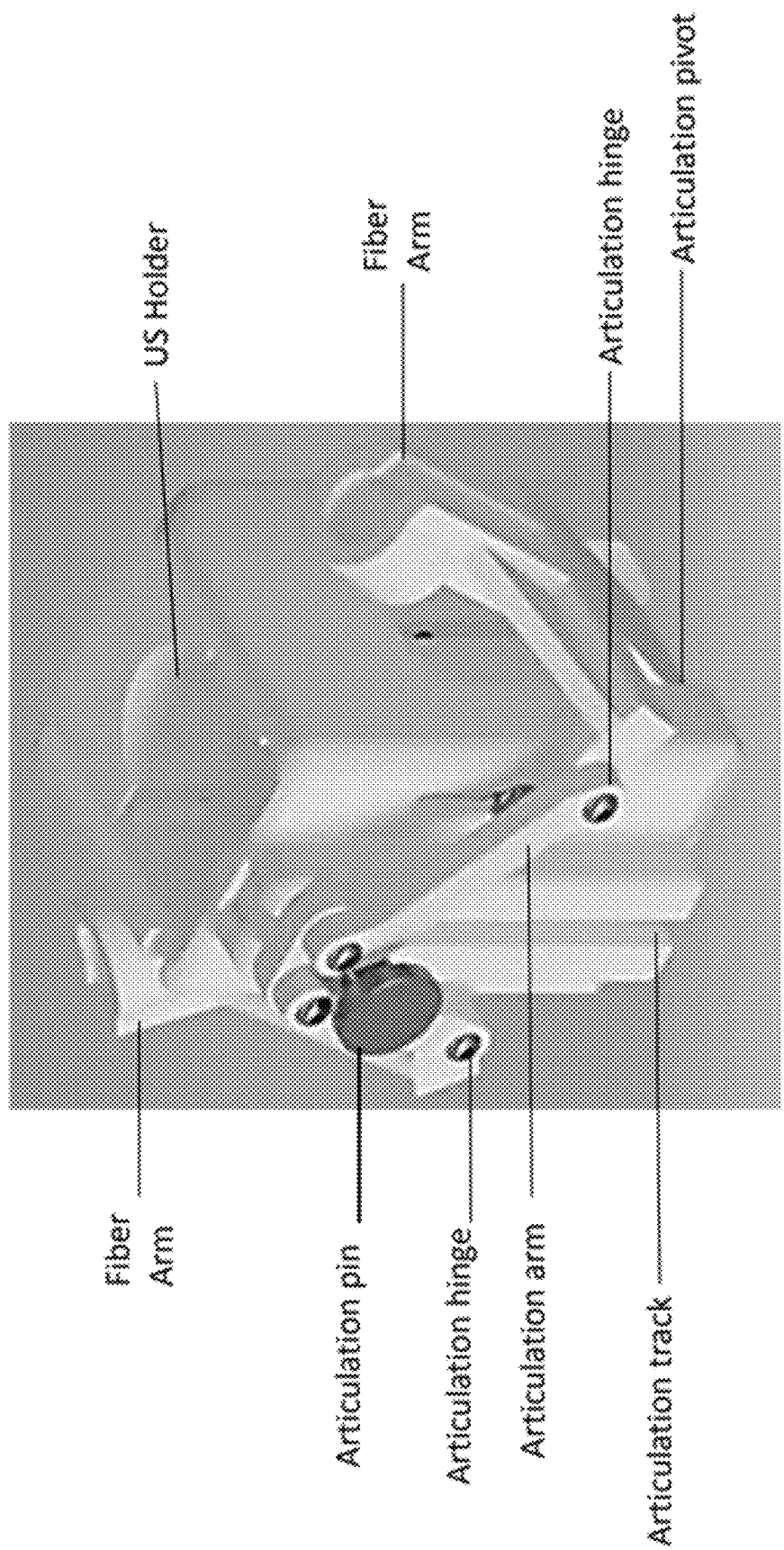
FIG. 3: Autodesk Inventor Design of a PAT holder consisting of fiber arms and ultrasound holder. This prototype allows articulation of the fiber arm through translation of articulation pin along the articulation track. Disadvantage of this approach is the fixed articulation pivot and coarse adjustment of fiber optic bundles.

Referring to FIG. 3, a prototype of PA probe bracket according to the present disclosure is provided. The PA probe has different articulation positions. The PA probe bracket includes two arms each configured to hold a bundle of fiber optic cable juxtaposed about a cavity that is configured to hold the US transducer. An articulation pin slides in an articulation track while it is coupled to articulation arms, which are coupled to fiber arms by articulation hinges. By sliding the articulation pin in the articulation track, each of the fiber arms articulate about a corresponding set of articulation pivots by being forced to articulate via the articulation hinge and the articulation arm. The caveat of this PAT holder is that it has fixed articulation pivot point and coarse adjustment of fiber optic bundles. What it needed is, for example, an adjustable vertical position of the articulation pin such that the fiber arms can be articulated from about 30° to about 90° with respect to a vertical line.

Figure 4:
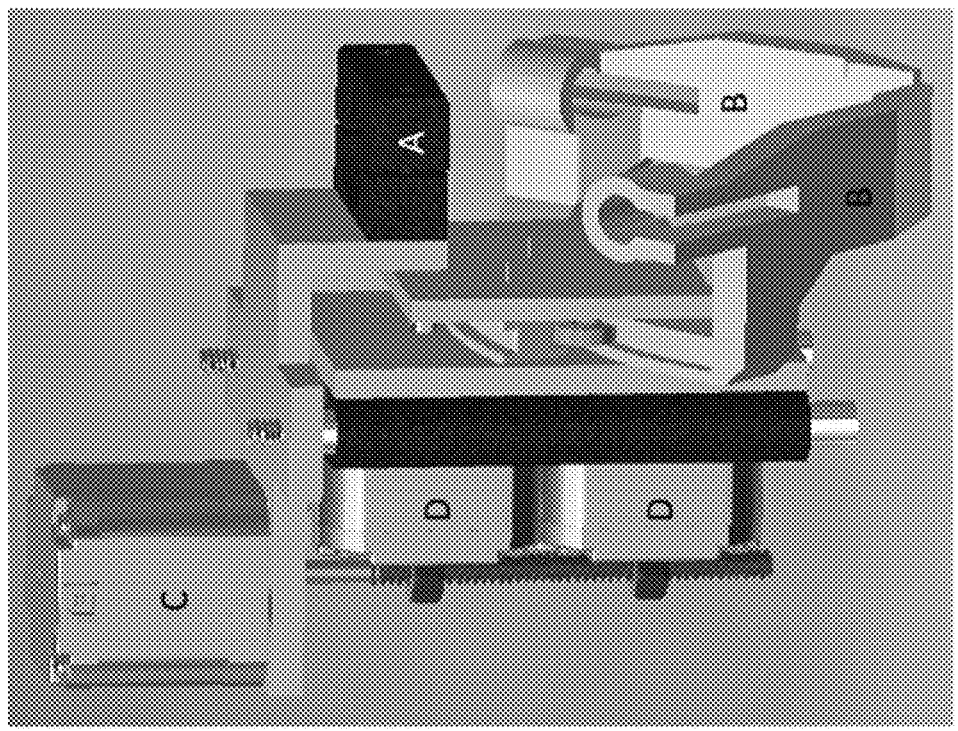
FIG. 4: Second prototype of PAT holder. This prototype consists of an ultrasound transducer holder (FIG. 4A), fiber optic bundle holders (FIG. 4B), and motors that allow translation of ultrasound transducer (FIG. 4C), and rotation of fiber optic bundles (FIG. 4D). The advantage of this prototype is that we can now finely tune the rotation fiber optic bundles and also move the ultrasound transducer to adjust the fiber bundle pivot point. The disadvantage of this prototype is too much material surrounding the fiber optic bundles that causes sub-optimal contact between the ultrasound transducer and fiber bundles.
Figure 5:
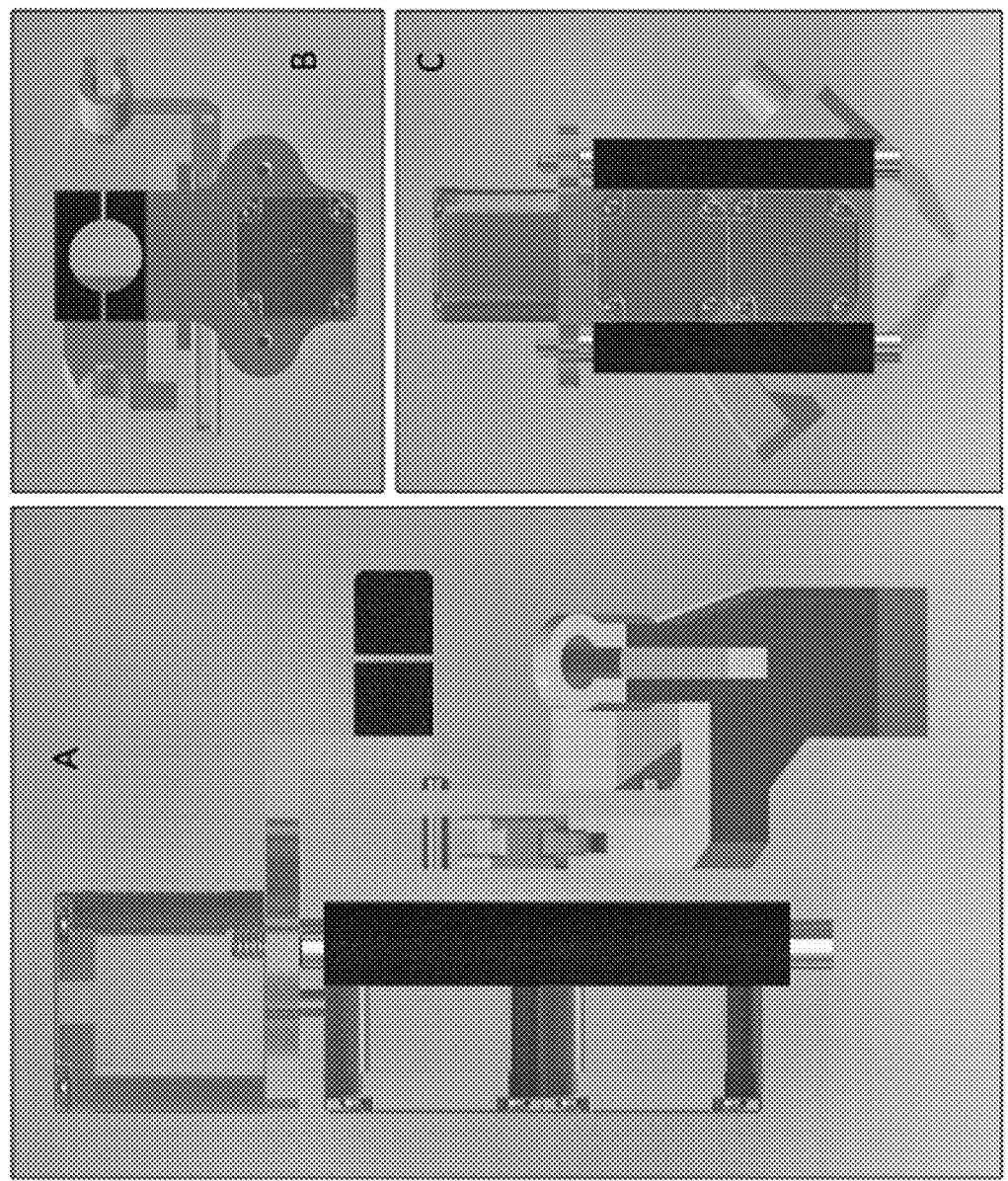
FIG. 5: Alternate views of prototype two of PAT holder consisting of side view (FIG. 5A), top view (FIG. 5B), and back view (FIG. 5C).

Referring to FIG. 4, yet another embodiment of PAT holder prototype is shown. Similarly to the first embodiment in FIG. 3, the prototype consisting of This prototype consists of a ultrasound transducer holder (A), fiber optic bundle holders (B), and motors that allow translation of ultrasound transducer (C), and rotation of fiber optic bundles (D). The advantage of this prototype is that we can now finely tune the rotation fiber optic bundles and also move the ultrasound transducer to adjust the fiber bundle pivot point. The disadvantage of this prototype is too much material surrounding the fiber optic bundles that causes sub-optimal contact between the ultrasound transducer and fiber bundles. FIG. 5A-5C shows alternative views of this second prototype PAT holder with side view (A), top view (B) and back view (C).

Figure 7A:
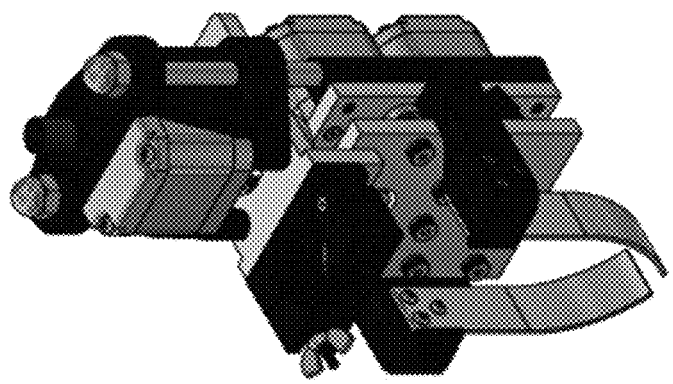
FIG. 7: Expanded (FIG. 7A) and constructed view FIG. 7 (B) of a third PAT holder prototype. This prototype has all of the features mentioned in prototype two, but the fiber optic bundle holders are designed to improve contact between the fiber optic bundles and ultrasound transducer. Fabricated parts are highlighted in gray, 3D printed parts are highlighted in black, and commercially available parts are highlighted in gold.
Figure 7B:
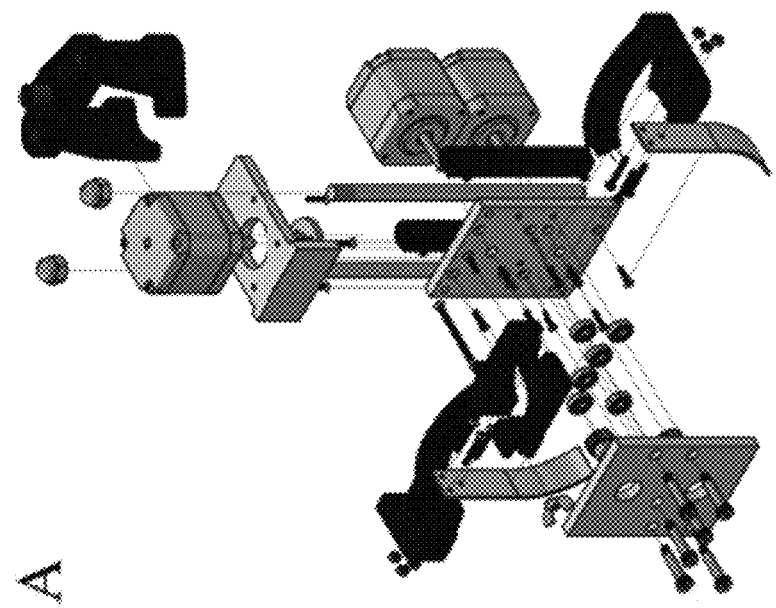

Referring to FIG. 7A-7B, yet another embodiment of a PA probe bracket is shown. 7A is an expanded view of this prototype and 7B is the constructed view. This prototype has all of the features mentioned in prototype two in FIG. 4, but the fiber optic bundle holders are designed to improve contact between the fiber optic bundles and ultrasound transducer. Fabricated parts are highlighted in gray, 3D printed parts are highlighted in black, and commercially available parts are highlighted in gold.

Figure 9:
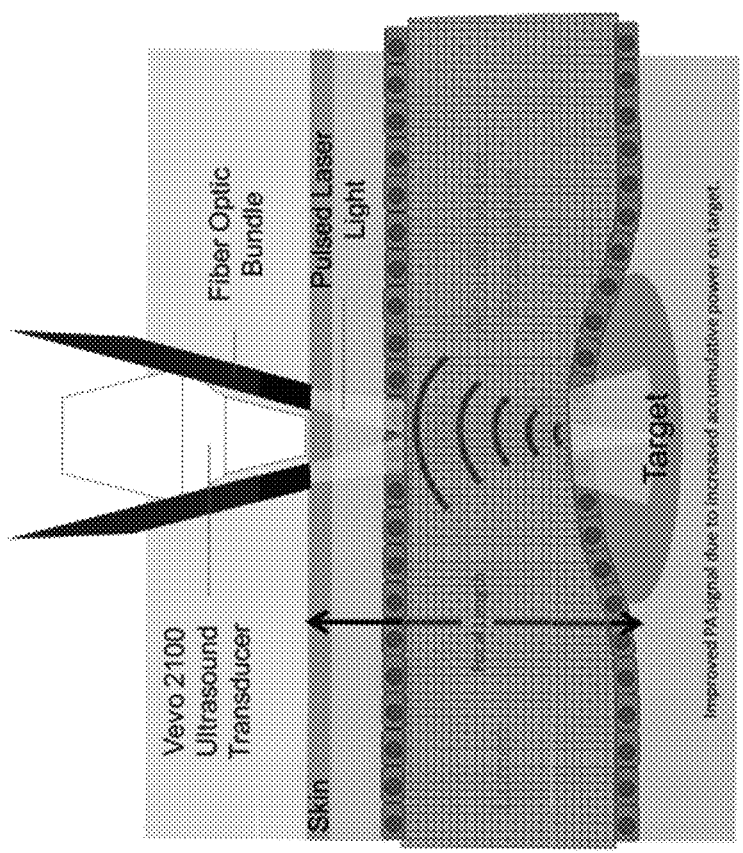
Figure 8:
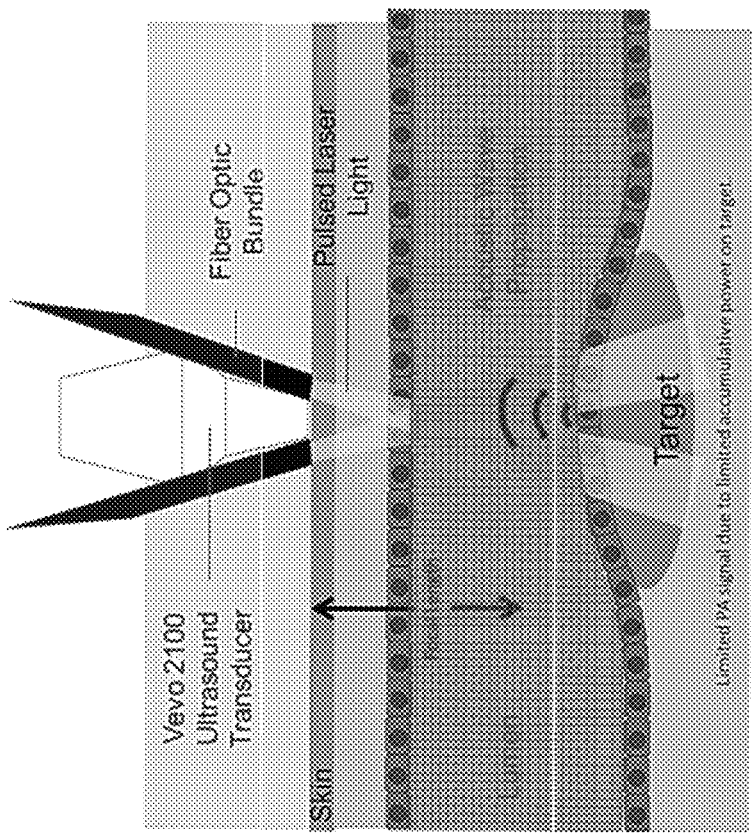
FIG. 8/9: Schematics showing advantages of in vivo focal length tuning. Focal length should be tuned based on user-specified region of interest. A sub-optimal focal length will cause light projections to converge away from the region of interest, therefore decreasing photon density in this region and also decreasing PAT signal generation (FIG. 8). Optimal focal length will maximize photon density in the region of interest to produce maximum SNR and potentially improving penetration depth (FIG. 9).

Achieving label-free, compositional specific imaging with high spatial resolution in deep tissue is considered to be a challenge in the field of optical imaging. Referring to FIGS. 8 and 9, the two pictures schematically show advantages of in vivo focal length tuning presented in this disclosure. Focal length can be tuned based on user-specified region of interest. A sub-optimal focal length is likely to cause light projections to converge away from the region of interest (target), therefore decreasing photon density in this region and also decreasing PAT signal generation (FIG. 8). Optimal focal length will maximize photon density in the region of interest to produce maximum signal noise ratio (SNR) and potentially improving penetration depth (FIG. 9).

The disclosure herein represents a PAT probe and US gel that can couple various sized transducers and fiber bundles while optimizing photoacoustic signal generation. Optimizing the light fluence as compared to state of the art PAT into tissue and minimizing light reflection off of the skin generates stronger PAT signal at depths of up to 1-1.5 cm, some even is optimistic for using PAT system to generate to 7 cm penetration depth, depending on the tissue of interest. This penetration is of importance as conventional optical techniques have a limited penetration depth on the order of 1 mm or less. The light shielding mechanism utilized in this disclosure eliminates PAT artifacts that obscure useful lipid information by preventing the probe-specific PA effects. Together, these advancements enhance in vivo lipid-based studies of atherosclerosis.

According to one embodiment of the present disclosure, incorporating photoreflectors into the US gel to reflect light back into tissue further enhances depth penetration. In one embodiment, titanium oxide or zinc oxide are incorporated as these compounds are active light reflecting ingredients in sunblock. In another alternative embodiment, silver nanoparticles are incorporated in the US gel as these have light reflection capabilities and have been previously fused with US gel.

In another embodiment, the probe bracket includes a compartment that contains the photoreflector infused US gel to prevent contact with incoming light. By optimizing this US gel, the probe can be shielded from reflected light and also redirect reflected light back into tissue.

Figure 10A:
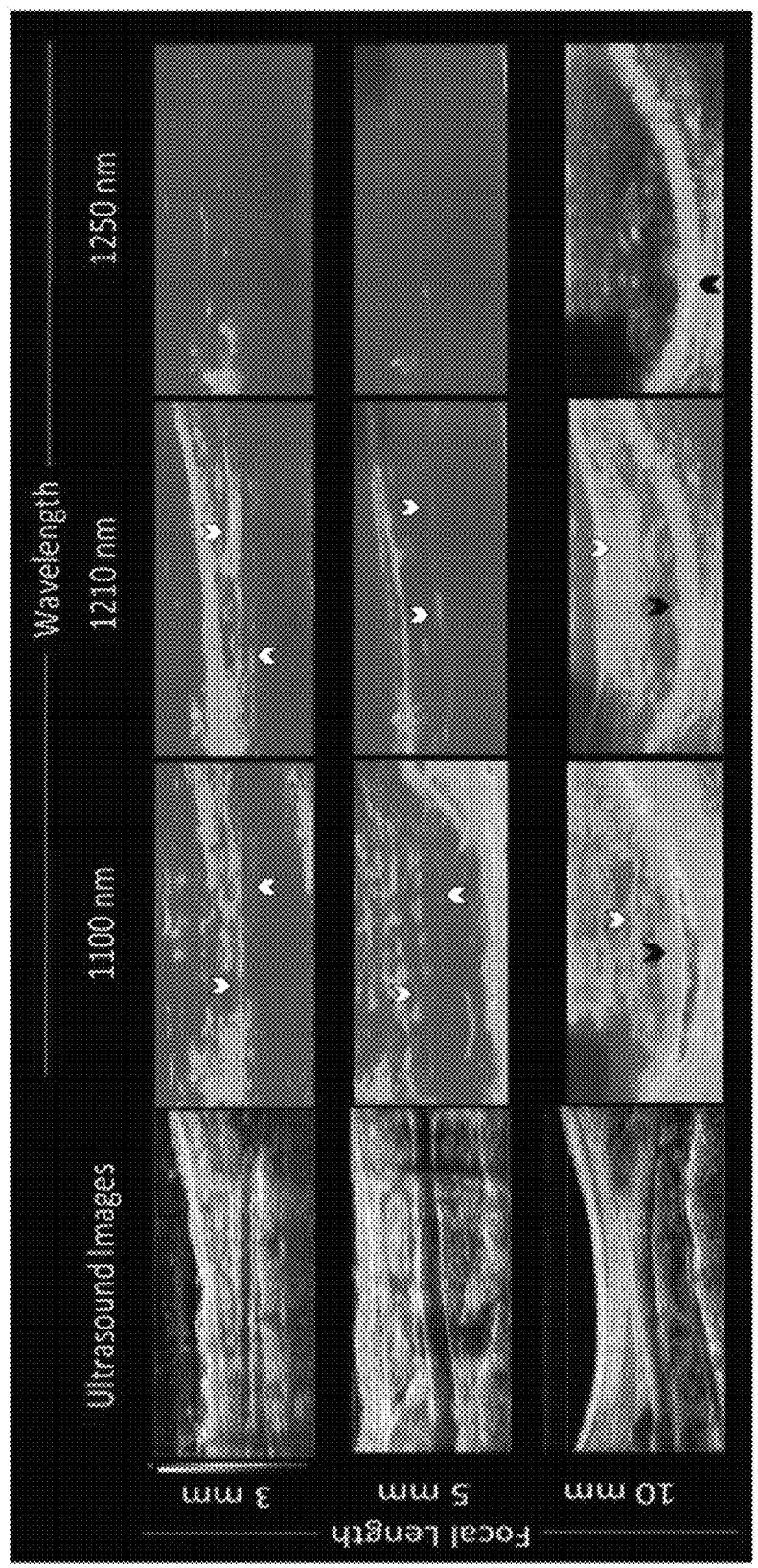
FIG. 10A: In vivo focal length tuning results of infrarenal aorta of apolipoprotein-E deficient mice using 1100 nm light to target blood, 1210 nm light to target lipids, and 1250 nm light as off-resonance control. We observed poor compositional contrast with 10 mm focal length, but began to resolve more signal with 5 mm focal length. 3 mm focal length produced the best results allowing user to resolve both anterior and posterior wall periaortic lipid accumulation. White arrows signify relevant compositional information and black arrows highlight reflection artifacts.
Figure 10B:
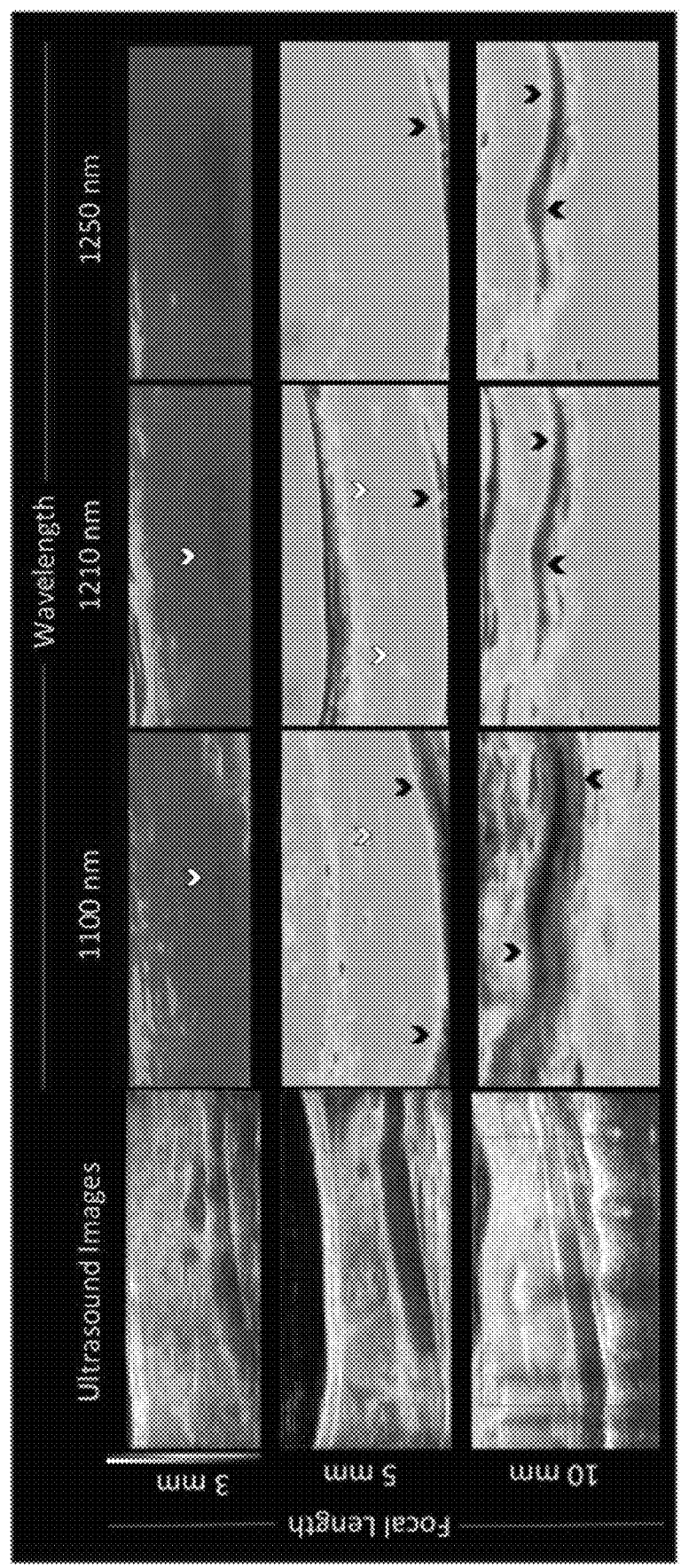
FIG. 10B: In vivo focal length tuning results of suprarenal aorta of apolipoprotein-E deficient mice using 1100 nm light to target blood, 1210 nm light to target lipids, and 1250 nm light as off-resonance control. We observed no compositional contrast with 10 mm focal length and minimal compositional contrast at 3 mm focal length. 5 mm focal length produced the best results allowing user to resolve both anterior wall periaortic lipid accumulation. White arrows signify relevant compositional information and black arrows highlight reflection artifacts.

Focal length is defined by the distance between skin of the subject of interest and about where the laser light from each of the fiber optic bundles intersects at a location below the skin. Referring to FIGS. 8 and 9, two different focal lengths can be achieved by articulating the angles of the fiber optic bundles. For example a more acute angle as shown in FIG. 8, provides a shallower focal length than a wider angle as shown in FIG. 9. By increasing the focal length and penetrating the tissue of interest, improved PA signal can be achieved due to increased accumulative power on target. Referring to FIGS. 10A and 10B, Long-axis in vivo ultrasound and PAT images of the infrarenal (A) and suprarenal (B) aorta in apoE$^{-/-}$ mice acquired using a 40 MHz central frequency transducer and 1100 nm (blood), 1210 nm (lipid), and 1250 nm (control) pulsed laser light are provided. PAT signal intensities correlate with the color bar shown on the top left. White arrow represents relevant PAT signal. Black arrow represents reflection due to skin surface. The signal is the greatest with a 3 mm focal length for the infrarenal aorta, and 5 mm for the suprarenal aorta. Therefore, adjustment of focal length help achieve the goal of investigating different depth tissue compositions.

Figure 15:
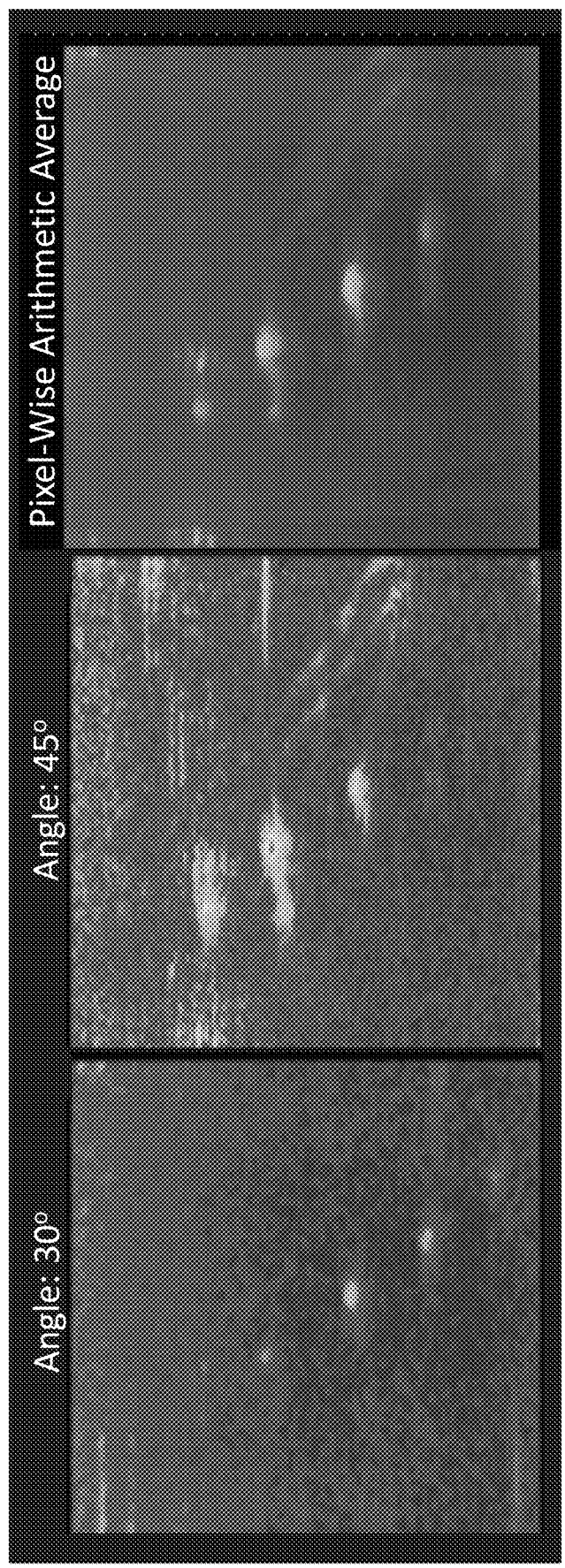
FIG. 15: PAT images of 20% PVA with 6 embedded PE-50 tubes. Fiber optic bundle angle, with respect to the ultrasound transducer, of 30° resolves deeper PE-50 tubes, and fiber bundle angle of 45° resolves more superficial PE-50 tubes. Using pixel-wise arithmetic averaging we can recreate an image that shows all 6 PE-50 tubes.

Disclosed herein also includes embodiments that using the PAT system to validate ex vivo and in vivo result. Referring to FIG. 12A, 20% Polyvinyl alcohol (PVA) phantom by weight embedded with six polyethylene-50 (PE-50) tubes was imaged at focal lengths of 2 mm, 3 mm, 5 mm and 6.5 mm. In a quantitative result plotted by PESO number against Signal Noise Ratio (SNR), it is clear that superficial PE-50 tubes has better SNR when using focal length of 2 mm and 3 mm; but for deeper PE-50 tubes, improved contrast is available using focal length of 5 mm and 6.5 mm. This validates the point that deeper tissues need longer focal length. For example, referring to FIG. 15, fiber optic bundle angle's change with respect to the ultrasound transducer, of 30° resolves deeper PE-50 tubes, and fiber bundle angle of 45° resolves more superficial PE-50 tubes. Using pixel-wise arithmetic averaging we can recreate an image that shows all 6 PE-50 tubes.

Similarly, referring to FIG. 12B, in vivo validation experiments show subcutaneous fat (close to skin) and infrarenal periaortic fat (deeper tissue) were imaged in apoE$^{-/-}$ mice to show increased PAT signal intensity when tuning focal length from 6.5 mm to 2 mm (panel A of FIG. 12B). The statistically difference of such SNR are shown in panels B and C of FIG. 12B.

Figure 14:
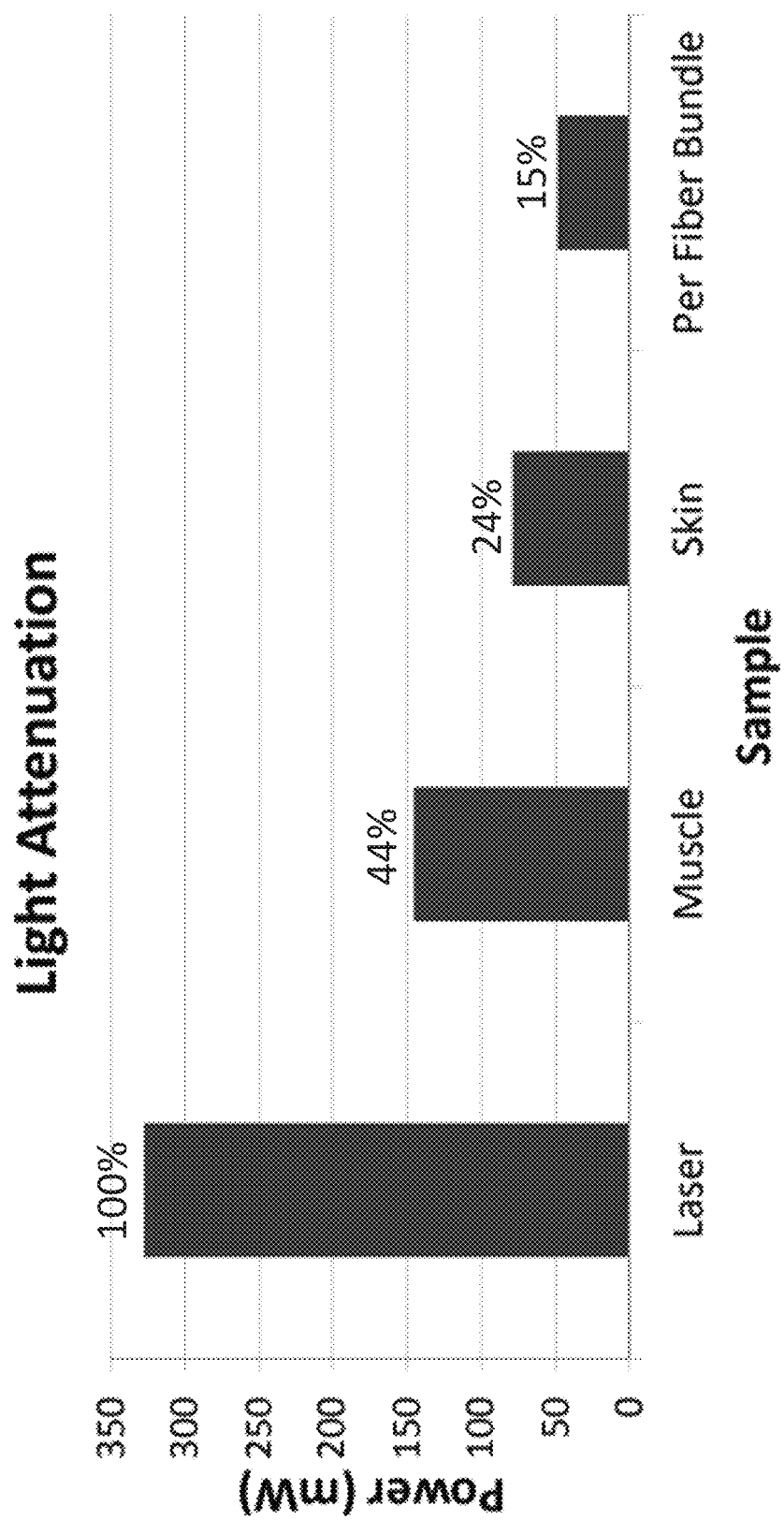
FIG. 14: Quantification of light transmittance through muscle, skin, and fiber optic bundle. Percent on bar graph represents the light transmittance through sample. Photon density through various layers can therefore vary, marking the need of creating methods to optimize light delivery to tissue.

Referring to FIG. 14, a quantification of light transmittance through fiber optic bundle, skin, and muscle is presented. Percent on bar graph represents the light transmittance through sample. Photon density through various layers can therefore vary, marking the need of creating methods to optimize light delivery to tissue.

In one alternative embodiment, one or more force sensors, e.g., capacitive sensors, known to a person having ordinary skill in the art, can be used with the PA probe bracket disclosed herein to measure force of the probe on the skin. The sensor(s) can be used as a feedback mechanism to automate positioning of the probe bracket. Without being limited by any theory, a feedback loop can be created to measure the force applied on the sample. Depending on penetration depth and SNR, the force on the sample can be increased or decreased to improve image quality.

Using image processing techniques one can seek to maximize US signal from a desired tissue by automatically maneuvering the fiber optic bundles (changing angle to effect focal depth) as well as the position of the US transducer.

In some embodiment, employing a light blocking effect material, such as aluminum filter, will greatly eliminate reverberation artifact in PAT signal.

Previous work has been done to utilize image processing and instrumentation engineering to improve image quality and eliminate PAT-specific artifacts. Nie et al. and Yu et al. have specifically utilized light redistribution methods to redirect reflected light back into tissue to increase photon density, thus improving signal intensity. While effective, the combination of this approach and also manually tuning the angle of the fiber optic bundles to improve optical density at various depths may be a superior method for improving image quality. Without being limited by the theory, we hypothesize that by increasing light penetration into tissue, by manipulating fiber-ultrasound orientation, we can improve the depth of penetration into tissue as well as signal to noise ratio.

Digital image processing techniques have also been used to minimize noise and remove artifacts. Singh et al. has used a PAFUSion technique to remove PAT reverberation artifacts. This approach uses the ultrasound transducer to acquired two images where one image is focused on the reflection artifact and the other is focused on the source of the artifact. A weighted addition is then performed to recreate an image without the reflection artifact. While effective, we present a simpler method to remove PAT reflection artifacts due to light reflecting off of the skin surface to cause a reflection artifact inducing PA effect at the probe face rather than within the sample. This PA ultrasound wave then travels and reflects off of the skin surface and is registered in the ultrasound system to originate two times the probe-skin distance. We hypothesize that we can place a light reflecting material on our PA probe to eliminate the probe face PA effect and effectively remove this probe-skin interaction artifact.

In sum, we establish a motorized photoacoustic tomography system for label free improvement in image quality. In this PAT probe system, the fiber optic bundles are finely tuned to increase photon density at various depths of tissues. We then use image reconstruction methods to obtain a better representation of PAT signal localization at various depths. Lastly, easily implemented solutions to PAT reverberation and pump-laser artifacts are provided to eliminate these issues at the source.

The Examples below are for illustrative purpose only. Those skilled in the art will recognize that numerous modifications can be made to the specific implementations described above and below. The implementations should not be limited to the particular limitations described herein. Other implementations may be possible.

EXAMPLES

Example 1. Photoacoustic System Design

Photoacoustic Tomography (PAT) has been shown to provide real-time compositional information of tissue without the need for exogenous contrast agents and with superior depth of penetration compared to conventional optical techniques. These previous optical barriers are overcome since PAT does not rely on conventional ballistic photons, but rather detects acoustic waves that are thermoelastically produced by photon-tissue interactions. Therefore, PAT can provide useful information that complements current clinical imaging modalities, thus emphasizing the capability of this technology to improve medical care. These characteristics highlight the potential of the technology to be used for a variety of biomedical applications ranging from lipid-based diseases, cancer, and peripheral nerve imaging.

While PAT has shown great potential, there are still certain biological barriers that have limited its use. For instance, applications for high-resolution noninvasive lipid-based imaging are limited to roughly 3 mm due to subcutaneous fat absorbers, as well as the intrinsic light attenuation due to optical properties of tissue. Therefore, there is still a need to optimize this technology to fully utilize its capabilities. Previous work has been done to utilize image processing and instrumentation engineering to improve image quality and eliminate PAT-specific artifacts. Light catching mechanisms have been particularly useful for redirecting reflected light back into tissue to increase photon density, thus improving signal intensity. While effective, the combination of this approach and manually tuning the angle of the fiber optic bundles to improve optical density at various depths (FIG. 1A) may be a superior technique for improving image quality. We hypothesized that by increasing light penetration into tissue through manipulating fiber-ultrasound orientation, we can improve penetration depth and signal-to-noise ratio (SNR). Our light-tuning hypothesis is dependent on fundamental photoacoustic principles that show that the initial photoacoustic pressure rise ($p_o$) results from light-induced thermoelastic expansion as characterized by equation (1).

$$p_o = \Gamma \mu_a F \quad (1)$$

This equation shows that $p_o$ is dependent upon the Grüneisen parameter ($\Gamma$), absorption coefficient ($\mu_a$), and optical fluence (F), assuming that all of the absorbed light is converted to heat energy. The Grüneisen parameter is defined by equation (2), where $\alpha$ is the isobaric volume thermal expansion coefficient, $\kappa$ is the isothermal compressibility, $\rho$ is the density of the sample, and $C_p$ is the specific-heat capacity.

$$\Gamma = \frac{\alpha}{\kappa \rho C_p} \quad (2)$$

These parameters, including $\mu_a$, are dependent on the innate tissue properties; therefore, we can assume that we can maximize PAT signal amplitude by increasing optical fluence density at various depths into the tissue. Taken together, we aim to design tunable fiber optic PAT probes that can enhance image quality for a wide variety of applications. Digital image processing techniques have also been used to minimize noise and remove PAT reverberation artifacts, however, many of these methods require computationally intensive algorithms or additional hardware. Singh et al., on the other hand, has developed a PAFUSion technique to remove PAT reverberation artifacts without the need of additional transducers or algorithms. This approach uses the ultrasound transducer to acquire two images where one image is focused on the reflection artifact and the other is focused on the source of the artifact. A weighted addition is then performed to recreate an image without the reflection artifact. While effective, we present a simpler method to remove PAT reflection artifacts due to light reflecting off of the skin surface to cause a reflection artifact inducing PA effect at the probe face rather than within the sample. This PA ultrasound wave then travels and reflects off of the skin surface, registering in the ultrasound system as originating two times the probe-skin distance (FIG. 1B). Without being limited to any theory, we proposed to apply a light reflecting material over our PA probe to eliminate the probe face PA effect and effectively remove this probe-skin interaction artifact.

The PAT system utilized in this study consists of a high-frequency small animal ultrasound system (Vevo2100, FUJIFILM Visual Sonics) and an Nd:YAG pulsed optical parametric oscillator (OPO) laser (Surelite EX, Continuum). Ultrasound system was equipped with a 40 MHz center frequency transducer (MS550D) that allowed the user to acquire US images with an axial resolution of 40 µm and PAT images with axial resolution of 124 µm. The Nd:YAG laser was capable of producing 5 ns pulses at 10 Hz ranging from 670-2500 nm. Pulsed light was delivered from the laser to the sample through a 2 meter fiber optic bundle with an opening diameter of 1.0 cm and rectangular terminals of 12 mm×2 mm. This allowed us to produce an optical fluence of 40 mJ, which is below the American National Standards Institute (ANSI) safety standards. A pulse generator (9200, Quantum Composers) synchronized laser excitation with ultrasound and PAT image acquisition by sending 1) appropriately timed 10 Hz, 5V inverted signals to the laser q-switch and flash lamp and 2) a normal 10 Hz, 5V pulse signal to the ultrasound system. This system design is summarized in FIG. 2.

Example 2. PAT Fiber-Tuning Apparatus Design

The PAT fiber-tuning apparatus was first designed using Autodesk Inventor Professional Student Edition and built using both 3D printed and fabricated 6061-T6 aluminum parts, as well as commercially available hardware. The 3D printed parts were printed from Acrylonitrile Butadiene Styrene plastic using a Stratasys Fortus 400mc 3D Production System (FIG. 7). The arms that hold fiber cables were made of 16-gauge-carbon steel, while the remaining plates that mount the stepper motors are made from 0.25" 6061-T6 aluminum (FIG. 7). A 12 V Nema 17 external linear stepper (17LS13-0404E-100H, StepperOnline), a 5.4V Nema 17 bipolar stepper (17HM15-0904S, StepperOnline), and a Stepoko 3-axis board (ROB-13899, SparkFun) were used to control the translation of the ultrasound transducer and rotation of the fiber optic bundles (FIG. 7). An external linear stepper motor specifically controlled the ultrasound transducer height by allowing a step angle of 1.8 degrees, thus producing a movement length of 0.02 mm per step. An independent bipolar stepper motor, equipped with a 16 tooth 32 pitch motor pinion gear that was able to produce a step angle of 0.9 degrees, controlled each fiber optic cable. These specifications were chosen to give us the appropriate strength, accuracy, and precise control of the fiber optic bundles and ultrasound transducer. These stepper motors were controlled by the Stepoko 3-axis board using Grbl software to allow us to finely tune the ultrasound and fiber optic bundle position. This apparatus was designed to have a 3 cm offset between the transducer face and motors to make sure that the hardware did not interfere with the experiments. Moreover, the translation of the ultrasound transducer allowed us to adjust the pivot point around which the fiber optic bundles rotated, giving us fine control over the focal length of the fiber optic bundles.

Example 3. Ex Vivo Validation Studies

A depth-profiling phantom was designed to evaluate the performance of our PAT holder. This phantom consisted of 20% Polyvinyl alcohol (PVA) by weight with six PE-50 tubes running through it at depths of 1 mm. Phantom mold was designed and optimized in Inventor and then 3D printed (Statasys Fortus 400mc). We used 20% PVA because of its acoustic and optical tissue mimicking properties. PE-50 tubes were used since they produce PAT signal when exposed to 1210 nm light. We prepared the PVA by using a modified method as described by Kharine et al. Briefly, 20% PVA was prepared by slowly dissolving PVA crystals in a secondary heat bath for 6 hours. Temperature of solution was cycled between 60° C. and 90° C. to promote dissolving of PVA crystals. Once dissolved, the 20% PVA solution was centrifuged to remove air bubbles. PVA was then poured into a phantom mold with PE-50 tubes and subjected to seven freeze thaw cycles. We defined one freeze thaw cycle as placing the mold in −20° C. refrigerator for 12 hours, followed by thawing the mold at room temperature for 12 hours. Once prepared, we imaged our phantom using combined ultrasound and PAT imaging. Short-axis B-Mode imaging was first used to identify all six PE-50 tubes. The PAT images using 1210 nm light to obtain PE-50 specific contrast was used to help quantify the focal length of our PAT probe to 2, 3, 5, and 6.5 mm. This process allowed us to acquire a cine loop as we tuned the depth with greatest photon density.

Figures 11A, 11B:
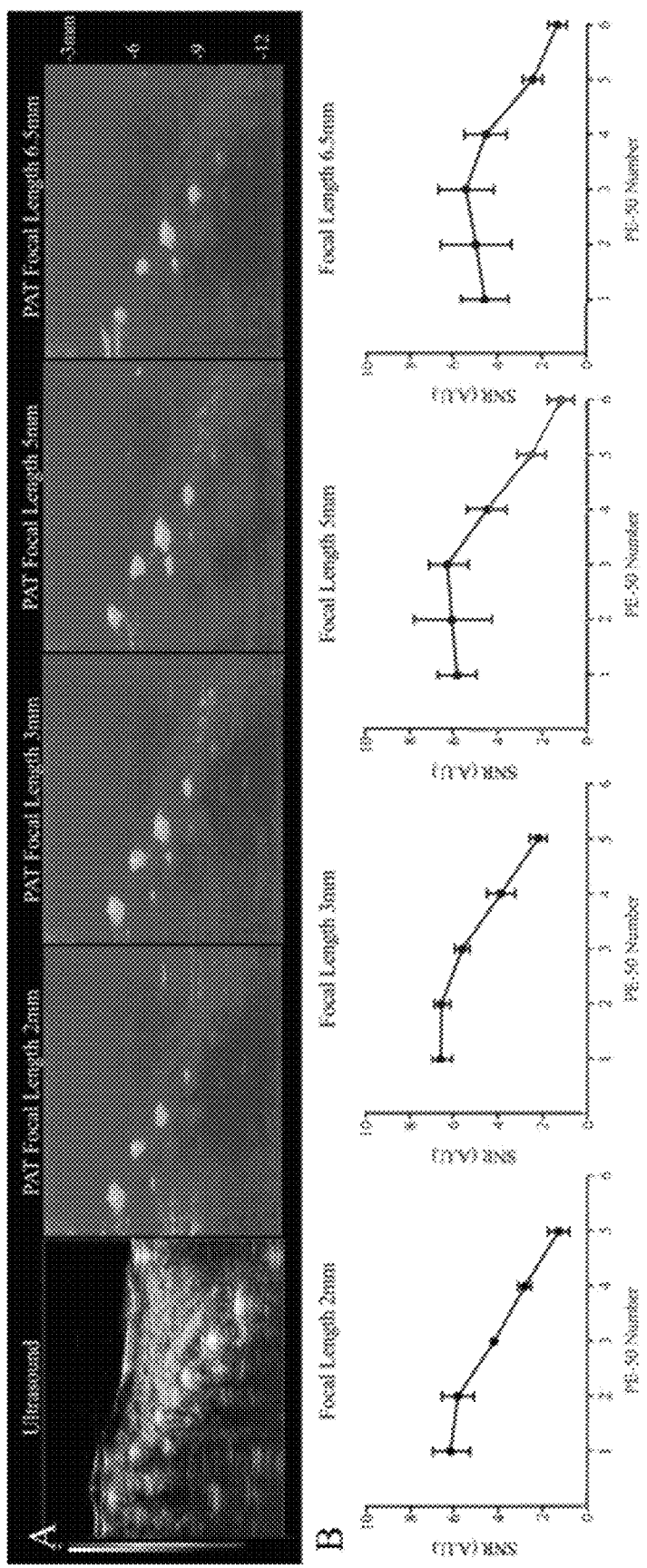
FIG. 11: Ex vivo Validation Results: Seven freeze-thawed cycled 20% PVA phantom embedded with 6 PE-50 tubes was imaged at focal lengths of 2 mm, 3 mm, 5 mm, and 6.5 mm (FIG. 11A). PE-50 tubes are highlighted with red dotted circles in the ultrasound image. Quantitative results show that we observe better SNR for superficial PE-50 tubes using focal length of 2 mm and 3 mm, and improved contrast for deeper PE-50 tubes using focal length of 5 mm and 6.5 mm (FIG. 11B).

FIG. 11 summarizes the results for the ex vivo validation experiments. Qualitative assessment shows that as we increase the focal length of our PAT probe from 2 mm to 6.5 mm we can resolve deeper PE-50 tubes that result in a penetration depth improvement of 2 mm (FIG. 11A). This improvement in image quality is supported by our quantitative SNR results, which show a focal length of 2 mm resolves the first four PE-50 tubes with SNR above 2.8, but resolves the fifth PE-50 tube with a poor SNR of 1.3, and no contrast for the sixth PE-50 tube. As we increase the focal length to 6.5 mm we see that we can slowly resolve contrast for the fourth, fifth, and sixth PE-50 tubes with SNR of 4.5±0.95, 2.4±0.44, and 1.3±0.42, respectively. Quantitative assessment of the SNRs also show that shorter focal lengths produce more optical contrast for the superficial PE-50 tubes, but we can improve SNR in deeper portions of the phantom by as increasing the focal length (FIG. 11B). Taken together, our ex vivo validation shows that the focal length of the PAT probe can be tuned based on specific needs of the user. In other words, shorter focal lengths should be used to resolve more superficial structures within a sample, while longer focal lengths should be used to resolve deeper structures within a sample.

Example 4. Photoacoustic Digital Image Reconstruction

The novelty of our approach allows us to not be limited by fixed fiber bundle positions, but rather allows us to tune the angles to maximize light fluency at various layers of tissue, thus allowing us to improve our depth of penetration and SNR ratio. To show this, we utilized median pixel averaging MATLAB algorithm to reconstruct our PAT images and obtain an image with maximal optical densities at various tissue depths. Briefly, median pixel averaging allows us to find the median pixel intensity from a stack of images with varying light focus. This approach allows us to minimize laser-induced noise, reduce averaging induced blurring, and obtain a better representation of PAT signal at various depths.

Example 5. In Vivo Validation Studies

We performed ultrasound and PAT imaging on the infrarenal aorta of apolipoprotein-E deficient mice (apoE$^{-/-}$) mice (n=3) to assess the performance of our PAT holder in vivo. ApoE$^{-/-}$ male mice were obtained from Jackson Laboratory (Bar Harbor, Me.), fed a standard chow diet, and weighed 24.7±4.9 grams at the time of imaging. A small animal anesthesia system (SomnoSuite, Kent Scientific) was used to anesthetize the animals using 2-3% isoflurane and 225 mL/min room air. Eye lubricate was applied to the eyes of the mouse to prevent corneal desiccation. Animal vital signs were closely monitored to ensure a consistent anesthetic plane. Mice were placed on a heated stage to maintain body temperature at approximately 34-36° C., which was monitored via rectal probe. Heart rate and respiration were monitored using electrodes built into heated stage and maintained at 500-600 beats per minute and 40-80 breaths per minute, respectively. Infrarenal aortas was found via long-axis B-mode imaging and imaging location was kept consistent between animals by identifying the left renal vein and tail artery bifurcation. The aorta was then imaged using 1210 nm light to target lipid, 1100 nm light to target blood, and 1400 nm as an off-resonance control Similar to our ex vivo studies, we then tuned the focal length of our PAT probe to 2, 3, 5, and 6.5 mm to acquire PAT images with different depths of max photon density. Images were analyzed in FIJI to calculate SNRs using a region of interest of 16 pixels due to small-scale thickness of the periaortic fat.

FIG. 12 summarizes the qualitative and quantitative in vivo assessment of our PAT holder. Image quality with the PAT holder was assessed at four focal lengths of 2, 3, 5, and 6.5 mm. Qualitative assessment shows increased signal intensity from subcutaneous and periaortic fat when imaging apoE$^{-/-}$ mice using 1210 nm light (FIG. 12A). Quantitative assessment shows steady increase of subcutaneous and perivascular fat SNR when tuning focal length from 6.5 mm to 2 mm. Specifically, we found subcutaneous fat SNR of 4.7±1.1 at 2 mm focal length, 4.0±0.41 at 3 mm focal length, 3.6±0.29 at 5 mm focal length, and 2.9±0.36 at 6.5 mm focal length (FIG. 12B). Additionally, we observed a periaortic fat SNR of 2.3±0.37 at 2 mm focal length, 2.1±0.25 at 3 mm focal length, 1.9±0.59 at 5 mm focal length, and 1.3±0.13 at 6.5 mm focal length (FIG. 12C). Our results also showed a statistically significant increase (p<0.05) in both subcutaneous and periaortic SNR between focal lengths of 2 and 6.5 mm. Overall, we observed a 62% increase in subcutaneous SNR and 77% increase in periaortic SNR, thus validating the importance of ultrasound transducer-fiber optic bundle orientation when optimizing PAT image quality. One limitation of this experiment is that the focal length was measured in air, not tissue. It is important to note that the focal length in tissue may vary due to varying scattering properties in various layers of tissue (i.e. skin, muscle, intestines). However, the results of these data suggest that the incident converging beam angles do play a role in obtaining optimal PAT contrast.

Example 6. Photoacoustic Reverberation Artifact Removal

The engineering design specification for materials that have the potential to reduce the PAT reverberation artifact include 1) complete reflection of light, 2) minimal attenuation of ultrasound and PAT signal, and 3) an inability to generate a PAT signal. We choose to experiment with aluminum filter with thickness of 4, 7, and 16 µm as aluminum is cost effective and its material properties allow reflection of light with no generation of PAT signal. We first tested the aluminum filter's ability to prevent light transmission by delivering pulsed laser light to the aluminum filter, with a power meter on the opposite side of a laser to measure light transmission. This was done to validate that the thin aluminum sheets did not have any major pinholes or defects that would prevent complete blockage of light. We then tested the aluminum filter's ability to remove PAT reverberation artifact in vivo by obtaining PAT images of periaortic fat on the infrarenal aorta of apoE$^{-/-}$ mice. The same animal care and imaging protocol was used as the in vivo PAT holder validation studies above. Both sides of the aluminum foil were coated with ultrasound gel to act as an acoustic coupling agent between both 1) the transducer and the foil and 2) the foil and the mouse. The transducer was then placed on the abdomen of the animal to obtain long-axis ultrasound and PAT images of the infrarenal aorta between the left renal vein and aortic trifurcation. We then imaged the mouse with and without the aluminum filter to assess the ability to remove reverberation artifact.

Figures 13, 13A, 13B, 13C:
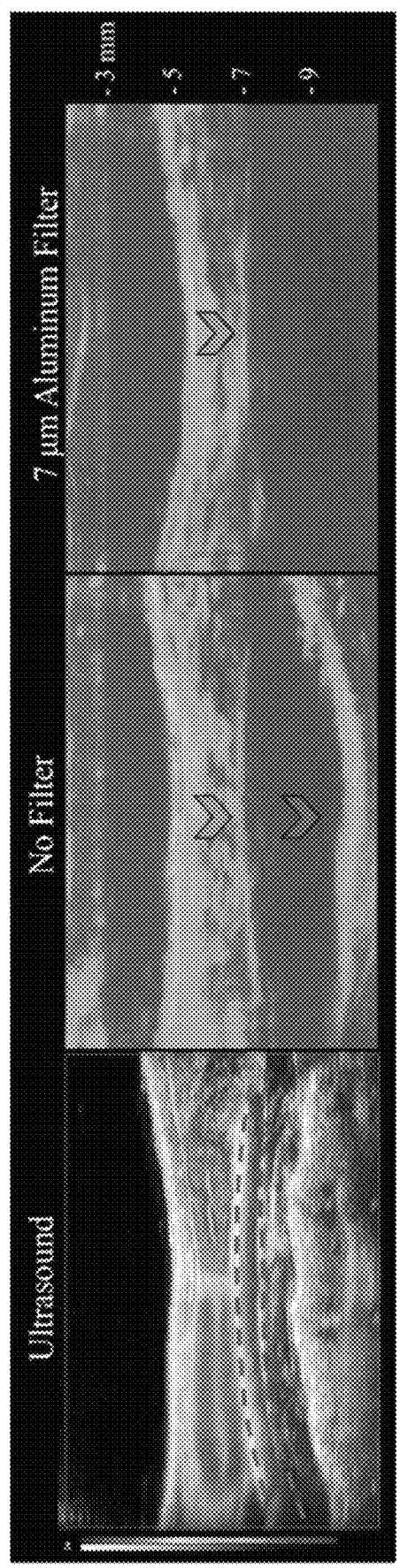
FIG. 13: Ultrasound FIG. 13A, PAT without filter (FIG. 13B), and PAT with filter (FIG. 13C). Infrarenal aorta highlighted in red dotted lines, periaortic signal highlighted by orange arrow, and reverberation artifact highlighted by red arrow. We can clearly see elimination of reverberation artifact through the light blocking effect of the aluminum filter.

We quantitatively assessed the ability of aluminum filters to completely reflect incoming light and also qualitative assessed the ability of these aluminum filters to prevent PAT reverberation artifacts. Through our light transmission experiment we found that all 4, 7, and 16 µm aluminum filters were able to completely block light transmission, thus showing potential to prevent PAT-related reverberation artifacts through decoupling of light-probe interactions. Moreover, when we applied our aluminum filter to our PAT probe and performed in vivo imaging of periaortic fat on the infrarenal aorta we found that the 4 and 7 µm aluminum filters (FIG. 13) prevent the PAT reverberation artifact. The 16 µm aluminum filter, however, did not allow acquisition of both ultrasound and PAT images as we hypothesize that it is too thick to allow penetration of acoustic waves. These experimental results show that 4 and 7 µm are thick enough to completely reflect light, yet thin enough to allow penetration of acoustic waves, making them effective filters to prevent probe-specific reverberation artifacts.

The invention claimed is:

1. A photoacoustic tomography (PAT) bracket comprising an ultrasound transducer; a holder, which holds and translates the ultrasound transducer; force sensors, which are coupled to the holder and provide information about a force applied by the ultrasound transducer on the skin of a subject of interest; and two rotating fiber arms coupled to the holder, wherein both rotating fiber arms are juxtaposed with respect to the holder at a pivoting point, and wherein each of the two rotating fiber arms to holds a fiber optic bundle and rotates the fiber optic bundle and laser light projections thereof such that the laser projections intersect at a selective focal depth of the subject of interest below the bracket.

2. The PAT bracket according to claim 1, wherein the holder holds and translates the ultrasound transducer to tune the pivoting point at which the two rotating fiber arms are juxtaposed with respect to the holder and at which each rotating fiber arm holds and rotates its fiber optic bundle and laser light projections thereof.

3. The PAT bracket according to claim 1, wherein the rotating fiber arms rotate the fiber optic bundles at an angle to converge the laser light projections at various depths of the subject of interest to optimize an optical contrast in the subject of interest.

4. The PAT bracket according to claim 1, wherein the holder translates the ultrasound transducer up and down with respect to the subject of interest.

5. The PAT bracket according to claim 1, wherein each of the two rotating fiber arms can articulate about the holder by angular motion, linear motion, or angular and linear motions.

6. The PAT bracket according to claim 1, further comprising a photoacoustic filter that is configured to redirect laser light reflected from the skin of the subject of interest back toward the skin while allowing ultrasound waves to pass through.

7. The PAT bracket according to claim 1, wherein the bracket further comprises an ultrasound gel incorporating photo reflectors to reflect light back onto the skin of the subject of interest.

8. The PAT bracket according to claim 1, wherein the fiber optic bundles transmit light at a fixed wavelength.

9. A method to generate optimum photoacoustic signals to a subject of interest, comprising:
   a. providing a photoacoustic tomography (PAT) bracket comprising an ultrasound transducer; a holder, which holds and translates the ultrasound transducer; and two rotating fiber arms coupled to the holder, wherein both rotating fiber arms are juxtaposed with respect to the holder at a pivoting point, and wherein each of the two rotating fiber arms holds a fiber optic bundle and rotates the fiber optic bundle and laser light projections thereof;
   b. applying a fixed wavelength of light through the fiber optic bundles while rotating the fiber arms and translating the holder to fine tune the pivoting point;
   c. acquiring photoacoustic images at different focal lengths in the subject of interest to obtain images with increased photon density at various depths; and
   d. applying digital image processing algorithms to concatenate all images obtained in (c) to construct a photoacoustic image with improved photon density throughout the photoacoustic image.

10. The method of claim 9, wherein the fixed wavelength is selected from the group consisting of 1100 nm, 1210 nm 1250 nm and 1400 nm.

11. The method of claim 9, which further comprises providing a light reflecting material over the ultrasound transducer to remove any reflection artifact that is potentially obscuring an image of the subject of interest, wherein the artifact is induced due to a photoacoustic effect at a face of the ultrasound transducer.

12. The method of claim 11, wherein the light reflecting material is a photoacoustic filter.

13. The method of claim 9, wherein the subject of interest is a lipid tissue, a cancerous tissue, a body fluid, a peripheral nerve tissue, or a polyethylene-50 (PE-50) tube.

14. The method of claim 9, wherein the focal lengths include 2 mm, 3 mm, 5 mm 6.5 mm or 10 mm for maximum photon density within the subject of interest.

* * * * *